United States Patent [19]

Covington et al.

[11] Patent Number: 4,567,006

[45] Date of Patent: Jan. 28, 1986

[54] METHOD FOR ENCAPSULATING MICROELECTRONIC SENSOR DEVICES

[75] Inventors: Arthur K. Covington, Newcastle upon Tyne; Alastair Sibbald, Tyne and Wear, both of England

[73] Assignee: Corning Glass Works, Corning, N.Y.

[21] Appl. No.: 617,271

[22] Filed: Jun. 4, 1984

Related U.S. Application Data

[62] Division of Ser. No. 366,722, Apr. 8, 1982, Pat. No. 4,502,938.

[30] Foreign Application Priority Data

Apr. 9, 1981 [GB] United Kingdom ............... 8111199

[51] Int. Cl.$^4$ ............................................. B29C 39/18
[52] U.S. Cl. .................................... 264/22; 264/40.1; 264/263; 264/272.16; 264/272.17; 264/510
[58] Field of Search ............. 264/139, 272.16, 272.17, 264/510, 511, 504, 22, 40.1, 263

[56] References Cited

U.S. PATENT DOCUMENTS

| 788,379 | 4/1905 | Rich | 264/504 |
|---|---|---|---|
| 2,004,465 | 6/1935 | Dietrichs | 264/139 |
| 3,560,601 | 2/1971 | Johnson et al. | 264/504 |
| 3,985,848 | 10/1976 | Frische et al. | 264/139 |
| 4,377,544 | 3/1983 | Rasmussen | 264/139 |

FOREIGN PATENT DOCUMENTS

| 2900114 | 2/1980 | Fed. Rep. of Germany | 264/272.17 |
|---|---|---|---|
| 2022502 | 12/1979 | United Kingdom | 264/139 |

*Primary Examiner*—James Lowe
*Attorney, Agent, or Firm*—W. J. Simmons, Jr.; A. L. Michaelsen

[57] ABSTRACT

A method of encapsulating microelectronic devices. A jet of gas is directed to an area of the device which is to remain free from encapsulating material. Polymerizable encapsulating material is then applied to the device. The material flows around the region upon which the jet impinges. The material is then cured.

4 Claims, 7 Drawing Figures

METHOD FOR ENCAPSULATING MICROELECTRONIC SENSOR DEVICES

This is a division of application Ser. No. 366,722, filed Apr. 8, 1982 now U.S. Pat. No. 4,502,938 issued Mar. 5, 1985.

FIELD OF THE INVENTION

This invention relates to a method of encapsulating field-effect transistor (FET) transducer devices.

The invention relates particularly to encapsulating microelectronic arrays of individual, selective, chemical-sensitive FET transducers for use in the separate or simultaneous detection and/or measurement of various chemical properties. ("Chemical properties", as used herein, shall be understood to include ion activity and concentration, presence and concentration of enzymes, substrates, antibodies, antigens, hormones and reducible gases and the presence, concentration and activity of any of a variety of chemical and biochemical substances including the constituents of enzymatic systems e.g. serum enzymes, glucose, lactates, pyruvates, creatinine, urea and the constituents of the immunochemical system).

There are many clinical situations, particularly in intensive care and during cardiac surgery, where a knowledge of blood pH and extracellular potassium activity (pK) can warn the clinician of impending problems. Blood pH is a useful indicator of respitory efficiency. The extracellular potassium level (which can vary rapidly) affects both heart rate and contractility, and can be critical in some cases. Knowledge of the activities of other ions, such as calcium and bicarbonate, is also useful in the clinical assessment of patients, and knowledge of the simultaneous activities of a plurality of ions is especially valuable as their concerted physiological action and interaction may permit more accurate diagnosis. A multiple function chemical transducer for this application would allow more precise computation of ionic activities because compensation could be made for imperfections in the selectivity of individual sensors by processing data from the transducer array in parallel.

DESCRIPTION OF THE PRIOR ART pH, pK and other ion activities can be measured with ion-selective electrodes, although the large, conventional types are not well suited to clinical application due to their expense, fragility, bulk, high electrical impedance and large volume deadspace. A number of various types of ion-selective electrodes are known, for example glass electrodes responsive to hydrogen, sodium, potassium and other ions in solution. Ion-selective electrodes are not restricted to glass as electroactive material; other solids such as lanthanum fluoride for a fluoride-responsive electrode (Frant, M. S., U.K. Pat. No. 1131 574 (1968); U.S. Pat. No. 3,431,182 (1969)), and a solution of the macrocyclic antibiotic valinomycin, in a suitable organic solvent, for a potassium-responsive electrode have been described (Simon, W., Swiss Pat. No. 479 870 (1969); U.S. Pat. No. 3,562,129 (1971)) and extensively used. Such electrodes, used in conjunction with a reference electrode to form an electrochemical cell, have high electrical impedances, which requires that electrical connections to the electrode be carefully screened and insulated to minimize external interferences, and that a high-impedance electronic circuit element such as a metal-oxide-semiconductor field-effect transistor (MOSFET) be used for signal amplification and/or processing. Great advantages accrue from the incorporation of the electroactive (ion-selective) material (glass, lanthanum fluoride, valinomycin or other) directly in contact with the active semiconductor device, thereby obviating such problems. The incorporation of several ion-sensitive sites on to a single array of microelectronic semiconductor devices with associated miniaturization offers unique advantages in terms of robustness, size, mass-fabrication potential, cost and application, with particular regard to biomedical usage.

Such devices, now known as ion-sensitive field-effect transistors (ISFETs), have been described in the scientific literature (Janata, J. and Huber, R. J., Ion-selective Electrode Rev, (1979), 1 31–79); the first report being that of Bergveld (IEEE Trans. Biomed. Eng., (1970), BME-17, 70-1) who suggested the use of a MOSFET transistor, without incorporation of the usual metal gate electrode, as a sensor for sodium ions and, later (IEEE Trans. Biomed. Eng, (1972), BME-109, 342–51), hydrogen ions in aqueous solution. In this instance, the gate insulation material (silicon dioxide, $SiO_2$) becomes hydrated after exposure to solution and functions in the fashion of a cation-responsive glass. However, hydration and ionic contamination of gate insulation material is a well-known cause of device instability and failure in the microelectronics industry where ion-barriers of silicon nitride and also ion-getters such as glasses incorporating pentavalent atoms, for example phosphorus, are used to minimize such contamination. The problems of gate-insulation contamination and also the gradual dissolution of $SiO_2$ adversely affect the quality of such devices as chemical sensors.

A further major difficulty lies in restricting, and isolating physically, the chemically-sensitive areas on the microelectronic device and maintaining the requisite electrical characteristics. For example, any electrical current flowing by the passage of charge-carriers between the electrical connections to the active device and the electrolyte in contact with the chemoresponsive areas compromises the stability of the device. The present state-of-the-art for device encapsulation is by crude methods such as brush encapsulation of epoxy resin under a microscope. The failure rate of devices fabricated by such techniques is high due to the penetration of electrolyte under the epoxy coating beyond the required boundary of the active area. This hand-application of insulating material is labour intensive and hence costly, and is incompatible with the highly sophisticated state-of-the-art for the mass production of electronic devices.

Attention is drawn to this problem, but it is not solved, in two more recent disclosures in this field (University of Utah, U.K. Pat. No. 1 529 743; Shimada, K., Matsuo, T. and Esashi, M., U.K. Pat. App. No. 2 010 011A). The first of these aforementioned disclosures concerns the use of electroactive materials other than hydrated silicon dioxide as the chemosensitive membrane used by ISFET devices. However, the formation of such films has been carried out by hand application under a microscope in a manner similar to that of the encapsulation material and is therefore not suited to the mass-production of chemosensitive microelectronic devices. The second of these disclosures is concerned with devices having a similar sectional structure to those in the first disclosure, but radically different plan geometry which confers an advantage insofar as the encapsulation technology is, to some extent, improved, but still requires a degree of manual involvement. However, two major shortcomings are thereby introduced; the process is not readily compatible with arrays of more than two devices selective to different chemical substances, and the extended, diffused source and drain regions, having high aspect ratios, greatly degrade the electrochemical sensitivity of the devices and introduce cross-modulation problems and furthermore greatly increase the overall temperature dependance of the output signal.

We assert that the electroactive materials used in the fabrication of chemosensitive microelectronic devices, and the manner of their application, must be compatible with mass production semiconductor technology for the successful development of microelectronic sensors of this nature. Furthermore, we consider the encapsulation material to be an important and integral part of the structure of the device, that the mode of application must be compatible with mass-fabrication technology, and that the resistance to water and ion penetration must be adequate in this context.

The aforementioned and other previous disclosures have been concerned with "enhancement-mode" devices; that is to say, devices where the source and drain regions are of a certain polarity and diffused into a substrate of opposite polarity. In order that such devices may function, a conduction pathway must be established between source and drain by the incorporation of an external voltage source in series with the potential reference electrode, in such a way that the device is biased correctly. Polarising potentials of this nature are highly undesirable for stable and reliable device performance as they contribute to charge-carrier movement in the electroactive membranes, encapsulation material and encapsulation/device interfaces. In contrast to previous disclosures, the present invention relates to devices operating primarily in "depletion-mode" or "enhancement/depletion-mode" (Sze, S. M., Physics of Semiconductor Devices, (1969), John Wiley and Sons Inc., p. 538) where a permanent, lightly doped conducting channel between source and drain, and of the same polarity, is provided by diffusion, use of an epitaxially grown film, ion-implantation or other means; such that no gate bias voltage is necessary for satisfactory operation.

SUMMARY OF THE INVENTION

The present invention is concerned with the solution of the aforementioned problems so that reliable, chemical-sensitive FET transducers can be achieved at relatively low cost by improvements in keeping with the highly developed methodology of the semiconductor industry, and provides a suitably encapsulated microelectronic array of chemosensitive FET transducers for detecting and measuring the chemical properties of the solution phase to which the device is exposed.

The method of the present invention relates to the encapsulation of microelectronic sensor devices. Such methods generally comprise applying to the device a polymerisable encapsulating material and effecting polymerisation thereof. The improvement of the present invention comprises restricting the area of application of the encapsulating material with an appropriately directed jet of gas to achieve selective encapsulation.

DESCRIPTION OF THE DRAWINGS

The objects and additional features of the present invention will become apparent from the following description taken in conjunction with preferred embodiments with reference to the accompanying drawings, in which.

DETAILED DESCRIPTION OF THE INVENTION

According to the present invention there is provided a suitably encapsulated array of chemosensitive field-effect transducers engineered for depletion-mode or depletion/enhancement-mode operation, and a means for the fabrication of the same using novel techniques and novel materials. The aforementioned array, fabricated on a single semiconductor element ('chip'), comprises a plurality of discrete ISFET devices all being similar in structure with the exception of the electroactive substance or substances employed as the chemically-responsive gate film by each device. We do not exclude from this specification an array of devices employing similar electroactive films for the purposes of increasing the accuracy of measurements, increasing the effective yield of device processing or other reason. Neither do we exclude the incorporation of other active or passive components on the same silicon element for the purposes of enhancing the performance or utility of the transducer array, such as signal multiplexers, amplifiers, compensatory devices or other elements.

Figure 1:
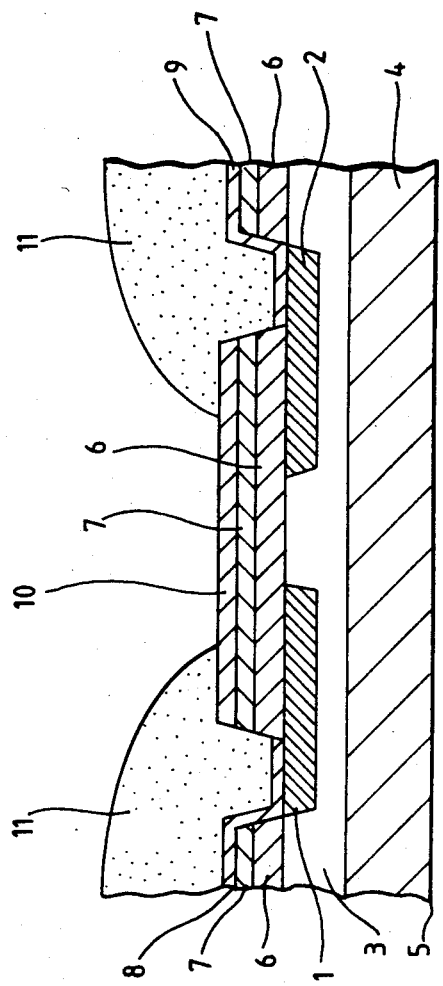
FIG. 1 shows a section diagram of a single, encapsulated depletion-mode chemosensitive device.
Figure 2A:
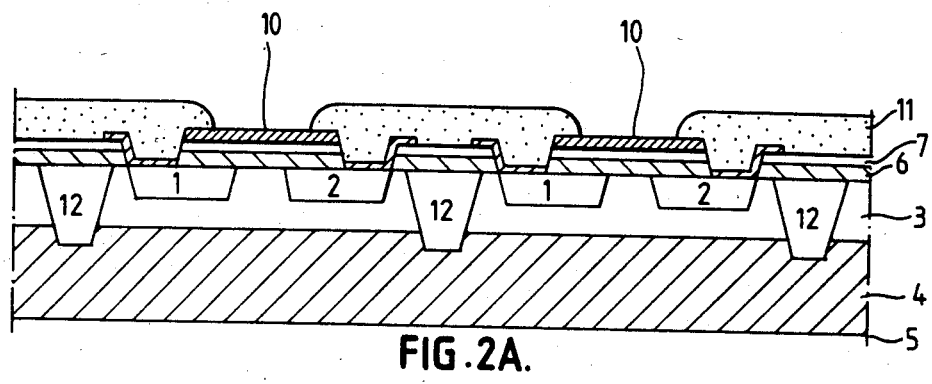
FIG. 2 shows section diagrams of three possible ways in which an array of depletion-mode chemosensitive devices may be engineered.
Figure 2B:
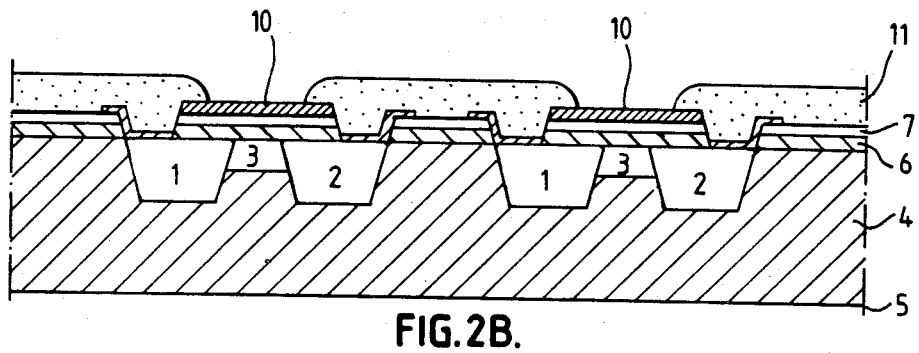
Figure 2C:
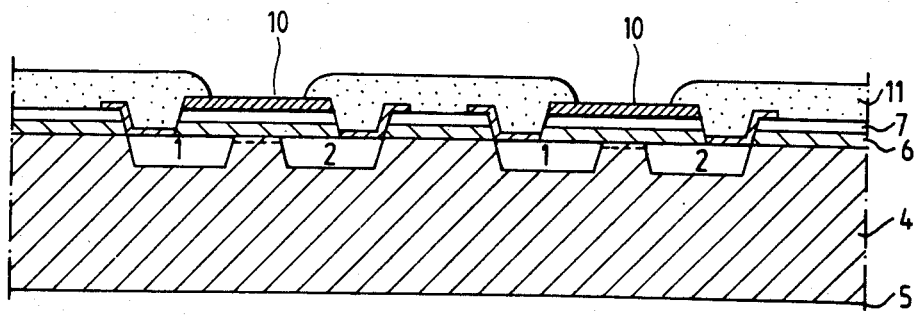

The following description, unless otherwise stated, pertains to a single device of which the aforementioned array is composed. The structure is shown in FIG. 1 in front elevation, and is characterized by two adjacent, diffused, semiconductor regions 1,2 with certain polarity created on a substrate 3 of the same polarity, such that the diffused regions are heavily doped (e.g. $10^{20}$ cm$^{-3}$) and permit ohmic, metallic connection, whereas the substrate material is only lightly doped (e.g. $10^{17}$ cm$^{-3}$) with impurities and therefore slightly electrically conducting. The substrate is mechanically supported by an insulator 4 as is common in state-of-the-art silicon-on-sapphire (SOS) technology, or on semiconductor material of the opposite polarity to the diffused and substrate material, such that a metallic back connection 5 may be established. When this particular method of fabrication is used to create a plurality of devices on the same silicon element (FIG. 2A) it is necessary to isolate individual devices with diffusions 12 deeper than, and of the opposite polarity to, the source 1, drain 2 and epitaxial layer 3, such diffusions being known as 'channel-stoppers'. Alternatively, the depletion-mode channel can be created by local diffusion (FIG. 2B), for example the source 1 and drain 2 regions may be heavily doped n-type material, the channel 3 lightly doped n-type material, and the semiconductor bulk 4 lightly doped p-type. A further technique sometimes used requires that the choice of processing materials and conditions is such that the surface of the bulk semiconductor is inverted (changed in polarity) and therefore lightly conducting (FIG. 2C).

The surface of the device is covered by an insulating oxide film 6 which is typically thermally grown $SiO_2$ and may be 50 nm thick over the channel between the diffused regions and 500 nm thick over the remaining surface. An ion-barrier film 7 is formed on top of the $SiO_2$, for example 50 nm of pyrolitically deposited $Si_3N_4$. Electrical connection is made to the diffused regions by etching holes through films 6, 7 using known photolithographic techniques and evaporating a metal film, typically aluminium 400 nm thick for connection to n-type silicon, to form contacts to the surface 8 and drain 9.

The composite gate insulator 6, 7 is coated with an electroactive material or materials 10 using well known thick-film or thin-film techniques; for example, doped polymer ion-selective membranes may be selectively deposited using a thick-film screening process; ion-selective glasses may be deposited through a photoresist mask using the relief photomask technique to define the areas of deposition. The device, or array of devices is affixed to a header, which may be a CERDIP, TO-5 metal pack or other suitable mount known to the microelectronics industry, and wire-bonding used to form electrical interconnections.

Figure 3:
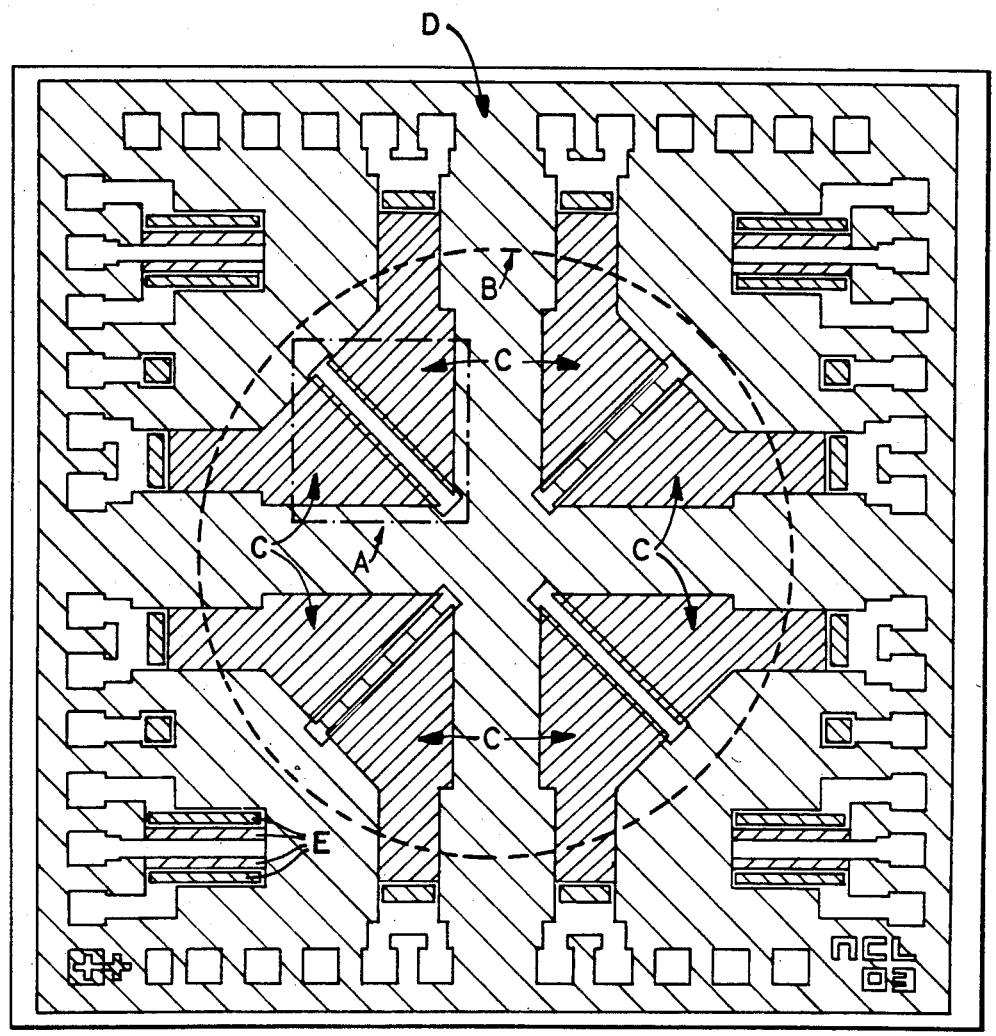
FIG. 3 shows the plan view of the geometry of a semiconductor element (NCL 03) which includes an array of four depletion-mode chemosensitive devices.
Figure 4:
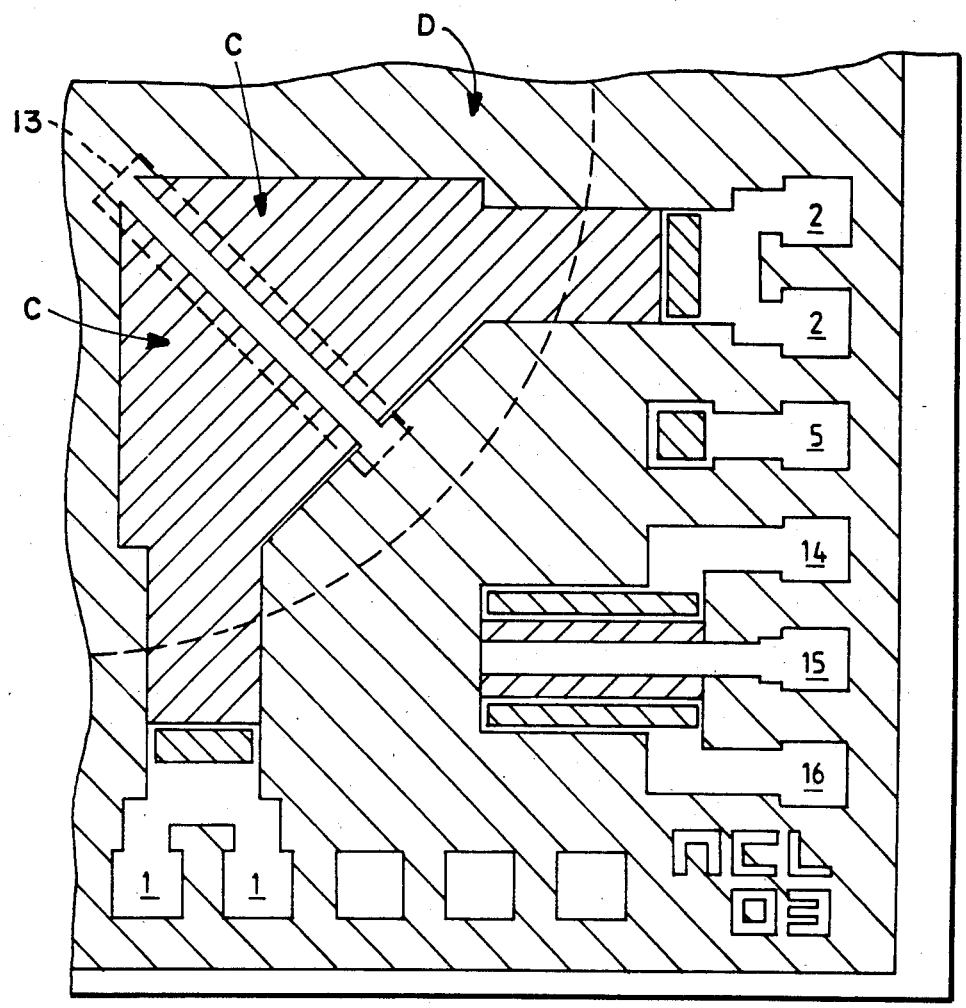
FIG. 4 shows the lower right-hand quadrant of the element shown in FIG. 3.

The bonding wires, header surface and chip periphery are sealed with a suitable encapsulating agent 11 in such a way that only the chemosensitive areas of the devices remain exposed; this process is detailed hereinafter and is facilitated by choosing an appropriate layout geometry for the device array, such as that shown in FIG. 3 which represents a plan diagram of the 3.9 mm square NCL 03 chip. More closely spaced cross-hatching lines which are designated capital C represent heavily doped n-type regions (n+); cross-hatching lines which are spaced further apart and designated capital D represent semiconductor bulk material (p−); closely spaced cross-hatching lines designated capital E represent contact holes through gate dielectric and ion-barrier films for electrical access by the metallization films, which are indicated by white areas, as will be readily appreciated and understood by those skilled in the art. The chip comprises four MOSFET devices and four chemosensitive devices all symmetrically orientated about an axis at 90°. Dotted circle B represents the encapsulant boundary, such that it surrounds the chemoresponsive areas of the four devices which must remain exposed while the rest of the chip is sealed during encapsulation. The square A represents the chemoresponsive area ('gate') of the device in the upper-left quadrant. FIG. 4 shows a quadrant of the chip in greater detail, where rectangle 13 represents a lightly doped channel region (3 in FIG. 2B); 5 is the bonding pad for connection to the semiconductor bulk; 14, 15 and 16 are the MOSFET bonding pads connected to source, gate and drain respectively. The bulk and source connections of the chemoresponsive devices may be joined to form a common leadout in order to reduce the number of electrical connections required, or the array may be designed to have a common source region, with a plurality of associated channels and drains.

An important aspect of the present invention is the encapsulating agent and means by which encapsulation is effected. Encapsulation is achieved by the use of materials such as Bis-GMA, and adduct of bis-phenol A and glycidyl methacrylate [2,2-bis(p-(2-hydroxy 3-methacryloxy propoxy)phenyl)propane], or Bis-GMA urethane adduct, which are polymerized by U.V. irradiation or other appropriate means, and restricted physically in the area of their application by an appropriate directed jet of air or inert gas. Such polymeric materials employed for encapsulation have been applied in dentistry for the sealing of occlusal surfaces where the problems of electrolyte penetration under, and through, the polymeric layer are also of primary consideration (Braden, M. et al, (1979), J. Dent., 7, (4), 275–303). The benefits of the use of this class of material are as follows:

(1) Adhesion of sealant to the substrate surface is enhanced by the penetration of resin into microfissures and surface defects (which can be deliberately introduced to 'key' the surface) thereby restricting lateral penetration by water and other solvents and furnishing electrically adequate encapsulation.

(2) The viscosity of the unpolymerized material can be controlled to be low enough to allow the material to flow around the active device, penetrating gaps and crevices in the device mount without damaging the fine (25 μm dia.) delicate wires bonded to the device for the purpose of electrical access, thus resulting in high processing yields.

(3) The materials, particularly those activated by U.V. irradiation, cure rapidly (<60 seconds) allowing rapid throughput for assembly-line encapsulation.

(4) The materials are biocompatible, which is advantageous for biomedical applications.

(5) The materials can be restrained in the area of their application by an appropriately directed jet of air or other gas, which permits the rapid and selective encapsulation of the peripheral areas of the semiconductor element whilst leaving the chemoresponsive gate areas exposed.

(6) The materials are relatively inert and resistant to leaching and ionic penetration, which would otherwise compromise the electrical insulation properties of the encapsulation and give rise to unreliable device performance or total device failure.

With regard to the latter claim, this has been confirmed by sealing 5 mm diameter discs of electrolytically chloridised silver (supported on Pyrex glass stems) with such materials, and also with typically used sealing/encapsulating agents (epoxy cements and silicon rubber), and storing the electrodes in 5% saline over an extended period (185 days). Frequent, intermittent monitoring of the effective leakage resistances of the electrodes (Table 1) confirms the superiority of the polymeric materials referred to over alternative agents most commonly used for ISFET encapsulation. In this context, we consider an effective leakage resistance of, or greater than, $10^9$ ohms to be desirable for the purposes of device encapsulation. Similar tests using a variety of aqueous solutions (N/100 NaOH, N/100 HCl, N/100 $CaCl_2$), show the material to be effective over a wide pH range (pH 2 to pH 12) and in the presence of calcium and chloride (Table 2).

TABLE 1

Effective leakage resistance of Ag/AgCl electrodes, sealed into Pyrex glass with various sealing/encapsulating agents, and stored in 5% saline for an extended period.

| Elapsed Time (days) | Effective leakage resistance (Ohms) | | |
| --- | --- | --- | --- |
| | Epoxy Resin | Silicon Rubber | Bis-GMA Encapsulant |
| 0 | $3.9 \times 10^{11}$ | $4.9 \times 10^{10}$ | $6.0 \times 10^{9}$ |
| 1 | * | $2.4 \times 10^{8}$ | $3.1 \times 10^{9}$ |
| 4 | $1.4 \times 10^{7}$ | $1.8 \times 10^{8}$ | $7.8 \times 10^{11}$ |
| 5 | | $9.8 \times 10^{7}$ | * |
| 7 | | $1.3 \times 10^{8}$ | $4.1 \times 10^{11}$ |
| 11 | | $8.7 \times 10^{7}$ | $5.8 \times 10^{11}$ |
| 185 | | $5.0 \times 10^{7}$ | $5.0 \times 10^{11}$ |

Key:
visual physical beakdown
*$10^{12}$ ohms, or greater

TABLE 2

Effective leakage resistances of Ag/AgCl electrodes, sealed into Pyrex glass with Bis-GMA material, and stored in various solutions.

| Elapsed time (days) | Effective leakage resistance (Ohms) | | |
| --- | --- | --- | --- |
| | N/100 NaOH (pH 12) | N/100 HCl (pH 2) | N/100 Ca Cl$_2$ |
| 0 | * | * | * |
| 1 | * | * | * |
| 4 | * | * | * |
| 5 | * | * | * |
| 7 | * | * | * |
| 11 | * | * | * |
| 185 | (not yet elapsed) | | |

Figure 5:
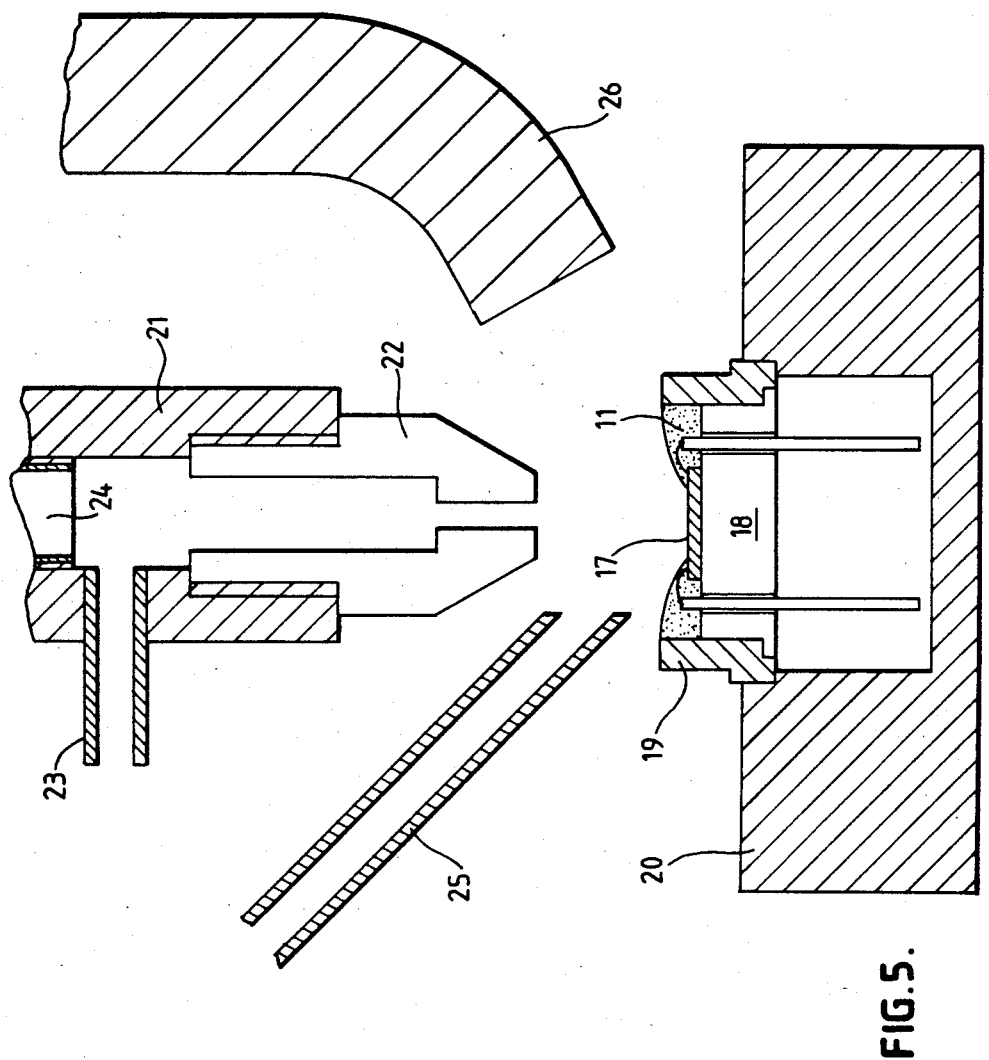
FIG. 5 shows an apparatus with which various semiconductor transducers, including those shown in FIGS. 1, 2 and 3 may be suitably encapsulated.

The application of such materials, and subsequent polymerization, is carried out in the following manner, and as shown by FIG. 5.

The microelectronic device array 17 is mounted onto a transistor or integrated-circuit header 18, as hereinbefore described with appropriate wire-bonded interconnections. A ring-type collar 19 is affixed to the header 18 and around the device 17. This assembly is temporarily mounted on a jig 20, being capable of movement in the horizontal plane using an x-y positioning drive, which is used to align the horizontally disposed semiconductor device surface underneath a jet of gas directed downwards onto, and orthogonally with respect to, the latter. The gas jet is supplied by a fixture 21 having a gas inlet port 23, a venturi 22 and a visible or near visible light source which may be a fibre-optic terminator 24. The following parameters have been found to be useful; gas flow rate, 0.5 l min$^{-1}$; venturi orifice, 0.75 mm; venturi to semiconductor distance 4 mm. Encapsulant material 11 is added to the inner edge of the restraining collar 19 with a hypodermic needle 25, whereupon the materials flows completely around the collar and perimeter of the device such as to envelope the metal wire-bonding and bonding pads, but the material is prohibited from flowing onto the centre of the device 17 by the radial, outward gas flow from the incident gas jet. The encapsulation material 11 is then rapidly polymerized by irradiation with U.V. light which may be appropriately directed through a U.V. transparent light-pipe 26, after which any unpolymerized surface material may be removed by a brief (3–5 second) ultrasonic rinse with iso-propyl alcohol or water. Modifications to this process are possible, and are not excluded from the scope of the present invention, for example the use of cyanoacrylate pretreatment to wet metal surfaces and promote more rapid flow-around; the pre-loading of collars with encapsulant before gas-jet application to speed up processing; the use of an integral light-pipe/gas jet assembly (drilled quartz rod); the use of alternative polymerisation techniques, such as chemical activation, where electroactive gate materials would be adversely affected by U.V. irradiation (i.e. valinomycin).

Furthermore, optical aids may be used to assist in the alignment of the gas jet with the chemoresponsive areas. Light from the fibre-optic source 24 is collimated by the gas-jet venturi 22 and provides a small illuminated area on the chip surface 17 which is, by necessity, accurately aligned with the central axis of the gas jet. The symmetrical structure of the device hereinbefore described (FIG. 3) is such that the optically induced drain currents flowing in the individual devices may be simultaneously processed electronically and the resulting information used to drive the aforementioned x-y positioner, and hence jig 20, thus optimally servocontrolling the position of the device with respect to the gas jet and allowing fully automatic encapsulation. This is a significant improvement on prior-art.

The present invention confers the following advantages:

(1) The centralised disposition of the chemoresponsive devices on the surface of the silicon element permits the use of the aforementioned, rapid and effective encpasulation system, the double-axis symmetry of the device enabling automatic control of the said system.

(2) The low aspect ratios of source 1 and drain 2 diffused areas ensure that the serial parasitic resistance associated with each individual device is minimal, which ensure optimal chemosensitivity and minimal thermal sensitivity. Additionally, the electrical interference between different devices in the same array is mininized.

(3) The style of the device array is compatible with known fabrication, mounting and testing techniques, and involves no further specialised equipment or skills for these purposes.

(4) The design is compatible with the addition of other semiconductor-based transducer elements or semiconductor devices for reasons of thermal, chemical or optical compensation, signal multiplexing, provision of pseudo potential-referencing systems or other purposes.

(5) The surface of the chemoresponsive film is not contacted by a conventional masking film, such as photoresist, and is therefore totally chemically uncontaminated.

(6) The absence of the requirement for a conventional mask eliminates at least two stages (those involving mask formation/application and mask removal) in the encapsulation process allowing rapid, high yield processing.

(7) The chemoresponsive film is not subject to any significant mechanical stresses or strains which might damage the film surface or impair adhesion to the semiconductor device.

(8) The area masked by the gas jet can be easily controlled and varied by altering the dimensions of the gas orifice, the gas flow rate (or viscosity) or the distance between the gas orifice and semiconductor device surface, thus allowing a variety of physically different devices to be processed by a single encapsulation system.

It must be noted that the selective encapsulation process and materials described hereinbefore are well-suited to the encapsulation of any semiconductor sensor, including other types of chemical transducers such as the OG-CHEMFET described in our British patent application No. 81 11198, gas sensors, pressure and temperature transducers and a variety of other devices or combinations thereof; we do not exclude any of these from the scope of the present invention.

Figure 6:
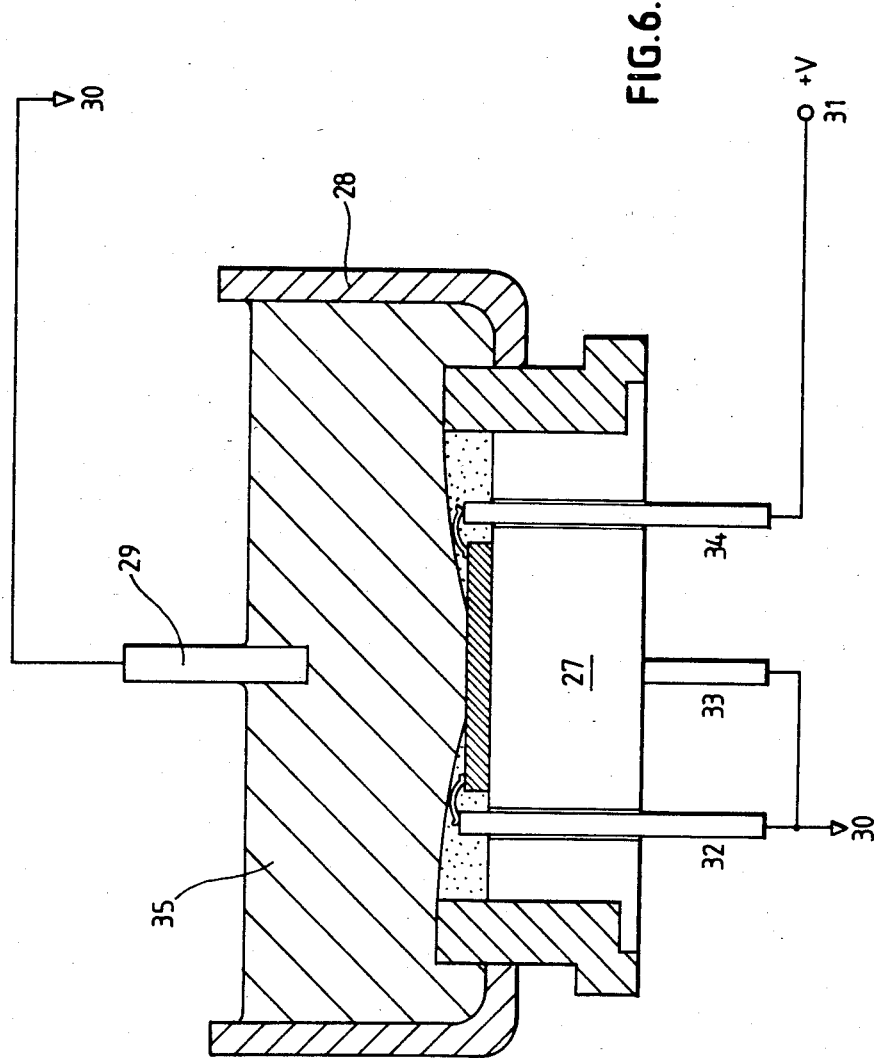
FIG. 6 shows the manner in which encapsulated depletion-mode chemosensitive devices may be used.

The method of application of encapsulated chemosensitive semiconductor device arrays is shown in FIG. 6, where the encapsulated device 27 comprises a header 18, device 17, collar 19 and encapsulating agent 11 as shown in FIG. 5. The device 17 is that described by FIG. 1 to 4. Considerations of a single element of the device array simplifies the following explanation. Lead out wires from the device source 32 and semiconductor bulk 33 are connected to ground 30. Drain connection 34 is connected to a low voltage source 31 (typically 2 to 5 V) and the device is exposed to the electrolyte sample under analysis 35, shown in this instance in an open cuvette 28. The electrolyte sample is grounded with a conventional reference electrode 29 which may be a calomel, porous-junction unit. No polarising voltage is necessary between reference electrode 29, and ground 30, as is required by previous disclosures concerned with enhancement-mode sensors.

The electrical potential in the bulk of the chemoresponsive film 10 (FIG. 1), with respect to the electrolyte, is determined by electrochemical reactions occuring at the film/electrolyte interface and is dependant upon the chemical properties of the latter. This potential, referred to the semiconductor bulk 4 via the reference electrode 29, controls the electrical charge density in the channel between source 1 and drain 2 regions, and hence the electrical current flowing between source and drain under the influence of the external voltage source 31. Thus the device effectively transforms a signal related to chemical properties directly into a low impedance current source.

Figure 7:
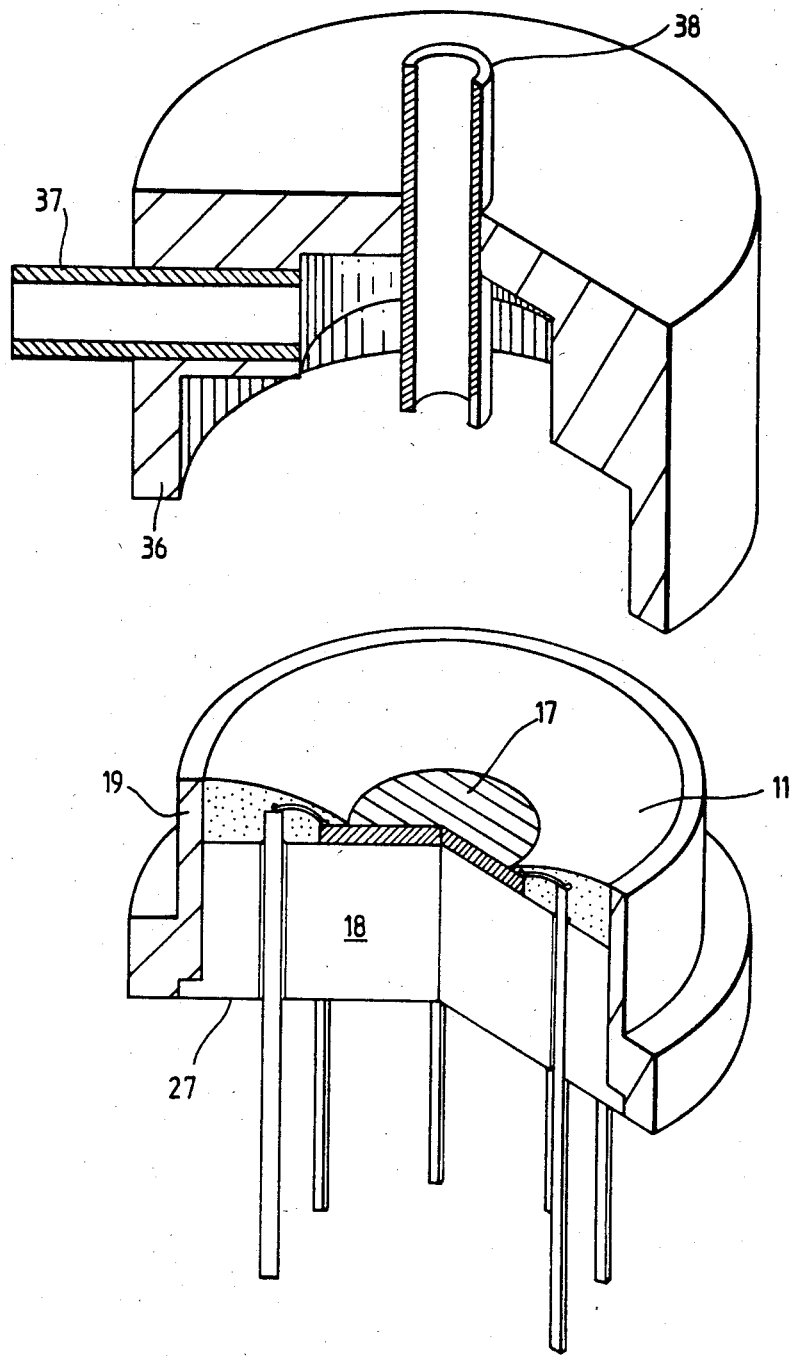
FIG. 7 is a partly sectioned, isometric drawing of the aforementioned device, together with a suitable flow-through cap.

The physical characteristics of the encapsulated devices render them ideal for flow-through sensor application. FIG. 7 shows an encapsulated device 27 as hereinbefore described, together with a flow-through cap 36 having fluid inlet 38 and fluid outlet 37 ports. A low pressure applied to 37 (with respect to 38) sucks fluid directly onto the sensor surface and provides an efficient flow-through assembly with small volume deadspace which is ideally suited for connection to an intravenous catheter for the purpose of continuous or intermittent ex-vivo, on-line blood analysis in conjunction with local, inexpensive signal processing/control hardware. This mode of operation is superior to in-vivo application for the following reasons.

(1) Ethical problems and objections associated with in-vivo use, such as that of blood clot formation, are virtually eliminated.
(2) Technical problems associated with in-vivo use are eliminated; for example it is known that intravascular sensors are frequently swept to the blood vessel wall and effectively screened from the main stream, being thus renedered inoperative.
(3) On-line calibration becomes possible, with the provision of extra inlet ports into the flow through cap.
(4) The need for an on-chip reference electrode is obviated.
(5) Several different sensor arrays may be used serially.

The physical nature of the encapsulated device 27 is also ideal for the mass production of single-function solid-state ion-selective electrodes, as the shape of the encapsulation material provides a former into which doped polymer films may be readily cast, using well-known materials and methodology, as will be appreciated by those skilled in the art.

We claim:

1. A method of encapsulating a microelectronic device comprising the steps of
    affixing a collar around said device,
    directing a jet of gas onto a predetermined area of said device that is to remain free from encapsulating material,
    flowing said encapsulating material into said collar, said material flowing around said region upon which said jet impinges, and
    curing said encapsulating material.

2. A method in accordance with claim 1 further comprising the step directing a beam of light along said jet so that said beam and said jet impinge upon the same region of said device.

3. A method in accordance with claim 2 further comprising the step of orienting said device in a horizontal plane to align a predetermined region on the surface of said device with said light beam.

4. A method in accordance with claim 3 wherein the step of curing comprises directing a beam of ultraviolet light onto said encapsulating material.

* * * * *